(12) United States Patent
Gilman et al.

(10) Patent No.: US 8,483,822 B1
(45) Date of Patent: Jul. 9, 2013

(54) ADAPTIVE MEDIUM VOLTAGE THERAPY FOR CARDIAC ARRHYTHMIAS

(75) Inventors: Byron L. Gilman, Edina, MN (US); Mark W. Kroll, Crystal Bay, MN (US); James E. Brewer, Sebeka, MN (US)

(73) Assignee: Galvani, Ltd., Edina, MN (US)

( * ) Notice: Subject to any disclaimer, the term of this patent is extended or adjusted under 35 U.S.C. 154(b) by 0 days.

(21) Appl. No.: 12/830,251

(22) Filed: Jul. 2, 2010

Related U.S. Application Data

(60) Provisional application No. 61/270,124, filed on Jul. 2, 2009.

(51) Int. Cl.
*A61N 1/00* (2006.01)

(52) U.S. Cl.
USPC ............. 607/5; 607/2; 607/18; 607/119

(58) Field of Classification Search
USPC ............................. 607/2, 5, 18, 119
See application file for complete search history.

(56) References Cited

U.S. PATENT DOCUMENTS

| | | |
|---|---|---|
| 3,703,900 A | 11/1972 | Holznagel |
| 3,923,060 A | 12/1975 | Ellinwood, Jr. |
| 3,952,750 A | 4/1976 | Mirowski et al. |
| 4,003,379 A | 1/1977 | Ellinwood, Jr. |
| 4,146,029 A | 3/1979 | Ellinwood, Jr. |
| 4,181,133 A | 1/1980 | Kolenik et al. |
| 4,222,386 A | 9/1980 | Smolnikov et al. |
| 4,280,502 A | 7/1981 | Baker, Jr. et al. |
| 4,349,030 A | 9/1982 | Belgard et al. |
| 4,390,021 A | 6/1983 | Spurrell et al. |
| 4,398,536 A | 8/1983 | Nappholz et al. |
| 4,408,606 A | 10/1983 | Spurrell et al. |
| 4,488,553 A | 12/1984 | Nappholz et al. |
| 4,488,554 A | 12/1984 | Nappholz et al. |
| 4,552,561 A | 11/1985 | Eckenhoff et al. |
| 4,559,946 A | 12/1985 | Mower |
| 4,572,191 A | 2/1986 | Mirowski et al. |
| 4,623,248 A | 11/1986 | Sperinde |
| 4,686,988 A | 8/1987 | Sholder |

(Continued)

FOREIGN PATENT DOCUMENTS

| | | |
|---|---|---|
| EP | 0540266 | 5/1993 |
| WO | WO 93/01861 | 2/1993 |

(Continued)

OTHER PUBLICATIONS 5,584,866, Dec. 1996, Kroll et al. (withdrawn). Gilman et al., "Applying the Principles of Functional Stimulation to Electrical CPR". 2008.
Gilman et al., "Electrically Induced Chest Constrictions Produce Verntilation As Well As Cardiac aOutput", Jan. 2008.

(Continued)

*Primary Examiner* — Nicole F Lavert
(74) *Attorney, Agent, or Firm* — Patterson Thuente Pedersen, PA

(57) ABSTRACT

Aspects of the invention are directed to advanced monitoring and control of medium voltage therapy (MVT) in implantable and external devices. Apparatus and methods are disclosed that facilitate dynamic adjustment of MVT parameter values in response to new and changing circumstances such as the patient's condition before, during, and after administration of MVT. Administration of MVT is automatically and dynamically adjusted to achieve specific treatment or life-support objectives, such as prolongation of the body's ability to endure and respond to MVT, specifically addressing the type of arrhythmia or other pathologic state of the patient with targeted treatment, a tiered-intensity MVT treatment strategy, and supporting patients in non life-critical conditions where the heart may nevertheless benefit from a certain level of assistance.

19 Claims, 8 Drawing Sheets

U.S. PATENT DOCUMENTS

| | | |
|---|---|---|
| 4,693,253 A | 9/1987 | Adams |
| 4,774,950 A | 10/1988 | Cohen |
| 4,823,800 A | 4/1989 | Compos |
| 4,830,006 A | 5/1989 | Haluska et al. |
| 4,945,909 A | 8/1990 | Fearnot et al. |
| 4,969,873 A | 11/1990 | Steinbach et al. |
| 4,986,270 A | 1/1991 | Cohen |
| 4,996,984 A | 3/1991 | Sweeney |
| 4,998,975 A | 3/1991 | Cohen et al. |
| 5,018,522 A | 5/1991 | Mehra |
| 5,041,107 A | 8/1991 | Heil, Jr. |
| 5,042,497 A | 8/1991 | Shapland |
| 5,087,243 A | 2/1992 | Avitall |
| 5,098,442 A | 3/1992 | Grandjean |
| 5,184,616 A | 2/1993 | Weiss |
| 5,193,535 A | 3/1993 | Bardy et al. |
| 5,193,537 A | 3/1993 | Freeman |
| 5,207,219 A | 5/1993 | Adams et al. |
| 5,220,917 A | 6/1993 | Cammilli et al. |
| 5,222,480 A | 6/1993 | Couche et al. |
| 5,230,336 A | 7/1993 | Fain et al. |
| 5,265,600 A | 11/1993 | Adams et al. |
| 5,282,836 A | 2/1994 | Kreyenhagen et al. |
| 5,282,837 A | 2/1994 | Adams et al. |
| 5,305,745 A | 4/1994 | Zacouto |
| 5,314,448 A | 5/1994 | Kroll et al. |
| 5,330,505 A | 7/1994 | Cohen |
| 5,330,506 A | 7/1994 | Alferness et al. |
| 5,330,509 A | 7/1994 | Kroll et al. |
| 5,336,245 A | 8/1994 | Adams et al. |
| 5,350,402 A | 9/1994 | Infinger et al. |
| 5,376,103 A | 12/1994 | Anderson et al. |
| 5,391,185 A | 2/1995 | Kroll |
| 5,411,524 A | 5/1995 | Rahul |
| 5,431,687 A | 7/1995 | Kroll |
| 5,431,688 A | 7/1995 | Freeman |
| 5,464,434 A | 11/1995 | Alt |
| 5,499,971 A | 3/1996 | Shapland et al. |
| 5,527,344 A | 6/1996 | Arzbaecher et al. |
| 5,601,611 A | 2/1997 | Fayram et al. |
| 5,607,385 A | 3/1997 | Francischelli et al. |
| 5,607,454 A | 3/1997 | Cameron et al. |
| 5,632,716 A | 5/1997 | Bui et al. |
| 5,658,237 A | 8/1997 | Francischelli |
| 5,662,689 A | 9/1997 | Elsberry et al. |
| 5,700,281 A | 12/1997 | Brewer et al. |
| 5,716,378 A | 2/1998 | Minten |
| 5,716,379 A | 2/1998 | Bourgeois et al. |
| 5,735,876 A | 4/1998 | Kroll et al. |
| 5,782,883 A | 7/1998 | Kroll et al. |
| 5,824,029 A | 10/1998 | Weijand et al. |
| 5,871,510 A | 2/1999 | Kroll et al. |
| 5,913,879 A | 6/1999 | Ferek-Petric et al. |
| 5,925,066 A | 7/1999 | Kroll et al. |
| 5,978,703 A | 11/1999 | Kroll et al. |
| 6,167,306 A | 12/2000 | Kroll et al. |
| 6,171,252 B1 | 1/2001 | Roberts |
| 6,185,457 B1 | 2/2001 | Kroll et al. |
| 6,230,056 B1 | 5/2001 | Kroll |
| 6,263,241 B1 | 7/2001 | Rosborough et al. |
| 6,298,267 B1 | 10/2001 | Rosborough et al. |
| 6,314,319 B1 | 11/2001 | Kroll et al. |
| 6,351,670 B1 | 2/2002 | Kroll |
| 6,438,419 B1 | 8/2002 | Callaway et al. |
| 6,556,865 B2 | 4/2003 | Walcott et al. |
| 6,560,484 B1 | 5/2003 | Kroll et al. |
| 6,567,697 B1 | 5/2003 | Kroll et al. |
| 6,577,102 B1 | 6/2003 | Vaisnys et al. |
| 6,760,621 B2 | 7/2004 | Walcott et al. |
| 6,853,859 B1 | 2/2005 | Kroll et al. |
| 7,011,637 B2 | 3/2006 | Sherman et al. |
| 7,035,684 B2 | 4/2006 | Lee |
| 7,488,293 B2 | 2/2009 | Marcovecchio et al. |
| 7,706,864 B2 | 4/2010 | Kroll et al. |
| 7,787,942 B2 | 8/2010 | Chinchoy et al. |
| 7,809,438 B2 | 10/2010 | Echt et al. |
| 7,957,799 B2 | 6/2011 | Sullivan et al. |
| 8,064,995 B1 | 11/2011 | Dupelle et al. |
| 8,121,681 B2 | 2/2012 | Hampton et al. |
| 8,160,703 B2 | 4/2012 | Stickney et al. |
| 8,165,662 B2 | 4/2012 | Cinbis et al. |
| 8,165,673 B2 | 4/2012 | Sherman et al. |
| 2002/0156503 A1 | 10/2002 | Powers et al. |
| 2002/0161407 A1 | 10/2002 | Walcott et al. |
| 2004/0039313 A1 | 2/2004 | Sherman et al. |
| 2004/0044373 A1 | 3/2004 | Kroll et al. |
| 2005/0197676 A1 | 9/2005 | Kroll et al. |
| 2006/0142809 A1* | 6/2006 | Kroll et al. .......... 607/5 |
| 2009/0177127 A1 | 7/2009 | Sherman et al. |

FOREIGN PATENT DOCUMENTS

| | | |
|---|---|---|
| WO | WO93/06866 | 4/1993 |
| WO | WO 93/19809 | 10/1993 |
| WO | WO97/15351 | 5/1997 |
| WO | WO99/03534 | 1/1999 |

OTHER PUBLICATIONS

Ristagno et al., "Transthoracic Applcation of Medium Voltage Therapy Maintains Forward Blood Flow During Cardiac Arrest", 2008.

Gilman, et al., Medium Voltage Therapy for Preventing and Treating Asystole and PEA and ICDs. 31st Annual Inernational Conference. Sep. 2009.

Wang et al, "Coronary Blood Flow Produced by Muscle Contractions Induced by Intracardiac Electrical CPR during Ventricular Fibrillation", Mar. 2009. vol. 32.

Wang et al, Transthoracic Application of Electrical Cardiopulmonary Resuscitation for Treatment of Cardiac Arrest. Crit Care Med. 2008, vol. 36, No. 11.

Koster, Limited 'hands-off' periods during resuscitation. 2003. pp. 275-276.

Snyder, "Wide variation in cardiopulmonary resuscitation interruption intervals amoung commercially available automated external defibrillators may affect survival despite high defibrillation efficacy", 2004. vol. 32, No. 9. pp. S421-S424.

Aufderheide TP, et al., "Death by hyperventilation: A common and life threatening problem during cardiopulmonary resuscitation." Wolf Creek VII, Ranch Mirage, CA Jun. 13-16, 2003.

Berg, RA et al., "Precountershock cardiopulmonary resuscitation improves ventricular fibrillation median frequency and myocardial readiness for successful defibrillation from prolonged ventricular fibrillation: a randomized, controlled swine study." Dec. 2002. vol. 40, Issue 6.

Cobb LA, et al., "Influence of cardiopulmonary resuscitation prior to defibrillation in patients with out-of-hospital ventricular fibrillation." JAMA Apr. 7, 1999; 281(13): 1182-8.

Eftestol T, et al., "Effects of interrupting precordial compressions on the calculated probability of defibrillation success during out-of-hospital cardiac arrest," Circulation May 14, 2002; 105(19): 2270-3.

Mr. Fell's Electrical Machine described, Gentleman's Magazine, Apr. 2, 1792.

Gilman, Byron et al., "Intracardiac Stimulation Produces Blood Flow During Ventricular Fibrillation," Cardiostim, Jun. 2008, 1 page.

Gilman, Byron et al., "Medium Voltage Therapy Produces Blood Flow for Prolonged Duration after Brief VF," HRS, May 2008, 2 pages.

Idris AH, et al., "Effect of ventilation on resuscitation in an animal model of cardiac arrest," Circulation Dec. 1994; 90(6): 3063-9.

KenKnight, Bruce H., et al. "Regional Capture of Fibrillating Ventricular Myocardium: Evidence of an Excitable Gap." Circulation Research, vol. 77, No. 4, Oct. 1995.

Gilman, Byron et al., "Electrically Induced Chest Constrictions Produce Blood Flow During Ventricular Fibrillation Via Thoracic-Only Pump Mechanism," HRS, May 9, 2007, 2 pages.

Gilman, Byron et al., "Electrically Induced Chest Constrictions During Ventricular Fibrillation Produce Blood Flow," ACC, Mar. 26, 2007, Presentation #1019-195, 2 pages.

Abstract, MacDonald RD, et al., "Impact of prompt defibrillation on cardiac arrest at a major international airport," Prehosp Emerg Care 2002; 6: 1-5.

Abstract, Menegazzi, JJ et al., "Immediate defibrillation versus interventions first in a swine model of prolonged ventricular fibrillation," Resuscitation Nov. 2003; 59(2): 261-70.

Menegazzi, JJ et al., "Ventricular fibrillation scaling exponent can guide timing of defibrillation and other therapies," Circulation Feb. 24, 2004; 109(7): 926-31.

Murdock et al., "Augmentation of Cardiac Output by External Cardiac Pacing: Pacemaker-Induced CPR," Pacing and Clinical Electrophysiology, Jan. 1986, vol. 9, No. 1, Part 1, pp. 1-154.

Niemann, JT et al., "Immediate countershock versus cardiopulmonary resuscitation before countershock in a 5-minute swine model of ventricular fibrillation arrest." Ann Emerg Med Dec. 2000; 36(6): 543-6.

Paradis, NA, et al., "Coronary perfusion pressure and the return of spontaneous circulation in human cardiopulmonary resuscitation," J Am Med Assoc 1990;.263: 1106-13.

Rosborough JP et al., "Electrical therapy for post defibrillatory pulseless electrical activity." PACE 2000 (NASPE abstracts) p. 591.

Abstract, Sherman, LD, et al., "Ventricular fibrillation exhibits dynamical properties and self-similarity," Resuscitation 2000; 47: 163-73.

Abstract, Steen, S et al., "The critical importance of minimal delay between chest compressions and subsequent defibrillation: a haemodynamic explanation." Resuscitation Sep. 2003; 58(3): 249-58.

Abstract, Stotz M, et al., "EMS defibrillation-first policy may not improve outcome in out-of-hospital cardiac arrest," Resuscitation 2003; 58: 277-82.

Valenzuela, TD, et al., "Outcomes of rapid defibrillation by security officers after cardiac arrests in casinos." N Engl J Med 2000; 343: 1206-9.

Van Alem AP, et al., "Interruption of cardiopulmonary resuscitation with the use of the automated external defibrillator in out-of-hospital cardiac arrest," Ann.Emerg Med Oct. 2003; 42(4): 449-57.

Walcott GP et al., "Effects of burst stimulation during ventricular fibrillation on cardiac function after defibrillation." Am J Physiol Heart Circ Physiol Aug. 2003; 285(2): H766-74.

Wang, HF, et al., "Effects of biphasic vs. monophasic defibrillation on the scaling exponent in a swine model of prolonged ventricular fibrillation," Acad. Emerg Med 2001; 8: 771-780.

Wang, Hao MD et al., "Electrically Induced Chest Constrictions Produce Ventilation as Well as Cardiac Output," NAEMSP, Jan. 2008, 3 pages.

Wang, Hao MD et al., "Transthoracic Application of Medium Voltage Therapy for Treatment of Cardiac Arrest," AHA, Nov. 2007, 2 pages.

Abstract, Wik, L et al., "Delaying defibrillation to give basic cardiopulmonary resuscitation to patients with out-of-hospital ventricular fibrillation: a randomized trial," JAMA Mar. 19, 2003; 289(11): 1389-95.

Abstract, Xie, J, et al., "Spontaneous gasping generates cardiac output during cardiac arrest," Crit Care Med Jan. 2004 : 32(1): 238-40. ScienceDirect. pp. 1-6. vol. 58. Issue 3. Sep. 2003.

Aufderheide, Tom P. M.D., "Pacemakers and Electrical Therapy During Advanced Cardiac Life Support," Respiratory Care Apr. 1995 vol. 40. No. 4.

Bleske, et al., "Comparison of adrenergic agonists for the treatment of ventricular fibrillation and pulseless electrical activity," Resuscitation 28, pp. 239-251, Aug. 1994.

DeBehnke, Daniel, "Resuscitation time limits in experimental pulseless electrical activity cardiac arrest using cardiopulmonary bypass," Resuscitation 27, pp. 221-229, Feb. 28, 1994.

Schuder, J. C., et al., "Transthoracic Ventricular Defibrillation in the Dog With Unidirectional Rectangular Double Pulses," Cardiovascular Research, 4, 1970.

Wik, L, et al., "Rediscovery of the importance of compressions to improve outcome," Resuscitation 2003; 58: 567-9.

EP Application No. 05852106.3, Search Report dated Oct. 28, 2008, 2 pages.

Love et al., Recommendations for Extraction of Chronically Implanted Transvenous Pacing and Defibrillator Leads: Indications, Facilities, Training. Apr. 2000. vol. 23. No. 4. Part 1. pp. 421-552.

Geddes, L.A., et al., "Electrically Produced Artificial Ventilation," Perspective and Progress vol. 22, No. 5, pp. 263-271 (1988).

Geddes, L.A., et al., "Ventricular Defibrillation With Single and Twin Pulses of Half-sinusoidal Current," Journal of Applied Physiology, vol. 34, No. 1, Jan. 1973.

Weng et al., A Novel Electrical Therapy for Postshock PEA in a Porcine Model and abstract. 2011.

Glenn, William W.L. et al., "Twenty Years of Experience in Phrenic Nerve Stimulation to Pace the Diaphragm," PACE, vol. 9, Nov.-Dec. 1986, Part I.

KenKnight, B.H., et al., "Regional Capture of Fibrillating Right Ventricular Myocardium Evidence of an Excitable Gap in VF Using High Resolution Cardiac Mapping," J.A.C.C., Feb. 1994, p. 283A.

Kirchhof, C., et al., "Regional Entrainment of Atrial Fibrillation Studied by High-Resolution Mapping in Open-Chest Dogs," Circulation, vol. 88, No. 2, Aug. 1993.

Kugelberg, J., "Ventricular Defibrillation—A New Aspect," Acta Chirurgica Scandinavica, Suppl. No. 372, 1967.

Kugelberg, J. E., "Ventricular Defibrillation With Double Square Pulse," Medical&Biological Engineering, vol. 6, 1968.

Laghi, Franco, et al., "Comparison of Magnetic and Electrical Phrenic Nerve Stimulation in Assessment of Diaphragmatic Contractility," Appl. Physiol. 80(5): 1731-1742 1996.

Leng, Charles T. M.D., et al., "Electrical Induction of Ventricular Fibrillation for Resuscitation From Postcountershock Pulseless and Asystolic Cardiac Arrests," Circulation pp. 723-728 (Aug. 7, 2001).

Murakawa, Yuji, et al. "The Effect of an Unsuccessful Subthreshold Shock on the Energy Requirement for the Subsequent Defibrillation." American Heart Journal, May 1989.

Quinn, et al., "Need for Sedation in a Patient Undergoing Active Compression—Decompression Cardiopulmonary Resuscitation," Academic Emergency Medicine, vol. 1, No. 5, pp. 463-467, Sep./Oct. 1994.

Resnekov, L., "Ventricular Defibrillation by Monophasic Trapezoidal-shaped Double-pulses of Low Electrical Energy," Cardiovascular Research, 2, 1968a.

Application and File History for U.S. Appl. No. 08/754,712, filed Dec. 6, 1996, Kroll et al.

Application and File History for U.S. Appl. No. 09/139,822, filed Aug. 25, 1998, inventors Kroll et al.

Application and File History for U.S. Appl. No. 09/251,553, filed Feb. 17, 1999, inventors Kroll et al.

Application and File History for U.S. Appl. No. 09/277,311, filed Mar. 26, 1999, inventors Kroll et al.

Application and File History for U.S. Appl. No. 09/964,111, filed Oct. 20, 2000, inventors Kroll et al.

Application and File History for U.S. Appl. No. 09/693,455, filed Oct. 20, 2000, inventors Kroll et al.

Application and File History for U.S. Appl. No. 09/393,443, filed Sep. 8, 1999, inventors Kroll et al.

Application and File History for U.S. Appl. No. 09/392,233, filed Sep. 8, 1999, inventor Kroll.

Application and File History for U.S. Appl. No. 08/931,233, filed Sep. 15, 1997, inventors Kroll et al.

Application and File History for U.S. Appl. No. 08/548,013, filed Oct. 25, 1995, inventors Kroll et al.

Application and File History for U.S. Appl. No. 08/548,014, filed Oct. 25, 1995, inventors Kroll et al.

Application and File History for U.S. Appl. No. 08/548,234, filed Oct. 25, 1995, inventors Kroll et al.

Application and File History for U.S. Appl. No. 09/139,216, filed Oct. 25, 1995, inventors Kroll et al.

Application and File History for U.S. Appl. No. 09/693,551, filed Oct. 20, 2000, inventors Kroll et al.

Application and File History for U.S. Appl. No. 10/429,509, filed May 5, 2003, inventors Kroll et al.

Application and File History for U.S. Appl. No. 11/053,177, filed Feb. 8, 2005, inventors Kroll et al.

Application and File History for U.S. Appl. No. 11/285,756, filed Nov. 22, 2005, inventors Kroll et al.

* cited by examiner

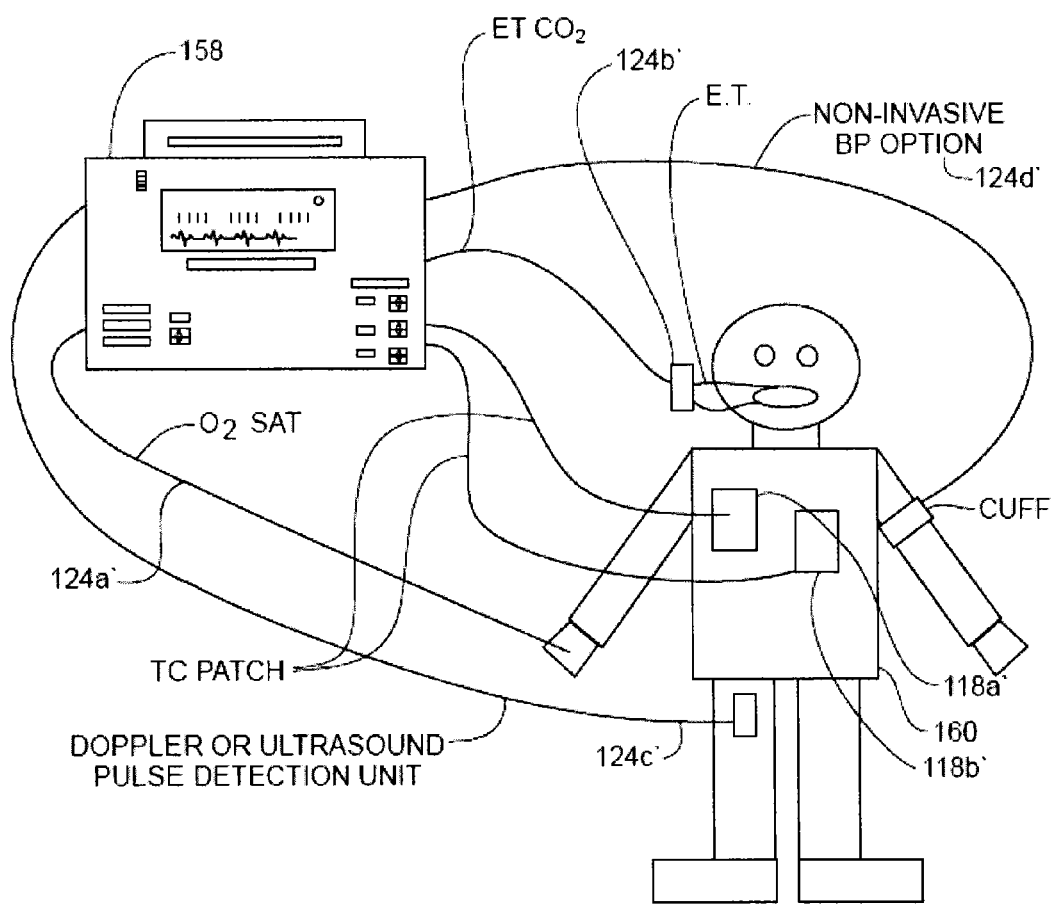

ADAPTIVE MEDIUM VOLTAGE THERAPY FOR CARDIAC ARRHYTHMIAS

PRIOR APPLICATION

This Application claims the benefit of U.S. Provisional Application No. 61/270,124, filed Jul. 2, 2009, entitled "Method and Apparatus for Providing Perfusion During VF, PEA and Asystole in External and Implantable Cardiac Devices," and further identified in its Application Data Sheet as "Medium Voltage Therapy for the Treatment of Cardiac Arrhythmias Including Pulseless Electrical Activity, Asystole and Ventricular Fibrillation," and which is incorporated by reference herein in its entirety.

FIELD OF THE INVENTION

The invention relates generally to treatments for individuals experiencing cardiac arrest and, more particularly, to implantable or external treatment apparatus and associated methods of operation thereof, for improving the applicability and effectiveness of medium voltage therapy (MVT) for a variety of patient conditions.

BACKGROUND OF THE INVENTION

Cardiac arrest is a significant public health problem cutting across age, race, and gender. A positive impact on cardiac arrest survival has been demonstrated with the substantial reduction in time to defibrillation provided by the widespread deployment of automated external defibrillators (AEDs), and the use of implantable cardioverter defibrillators (ICDs) and implantable pulse generators (IPGs). Examples of AEDs are described in U.S. Pat. Nos. 5,607,454, 5,700,281 and 6,577,102; examples of ICDs are described in U.S. Pat. Nos. 5,391,186, 7,383,085, and 4,407,288, and examples of IPGs are described in U.S. Pat. Nos. 4,463,760, 3,978,865, and 4,301,804, the disclosures of which are incorporated by reference herein.

Optimal resuscitation therapy for out of hospital (OOH) cardiac arrest is the subject of substantial ongoing research. Research has been clear in demonstrating that the timing of resuscitation is of critical importance. For example, there is less than a 10% chance of recovery just ten minutes after the onset of ventricular fibrillation (VF). This knowledge led to the recent widespread deployment of AEDs, primarily in public areas with a high population concentration such as airports and shopping malls. A positive impact on cardiac arrest survival has been demonstrated due to the substantial reduction in time to defibrillation as a result of more available access to AEDs. In addition, for those patients identified as being at particularly high risk, an implantable cardioverter-defibrillator is often implanted in order to address episodes of cardiac arrest without the involvement of a rescuer.

In the case of VF, performing CPR-type chest compressions before defibrillation and minimizing the time to defibrillation shock following the cessation of the CPR chest compressions is important in facilitating effective recovery especially in cases of long duration VF. It is generally believed that perfusion of the myocardium achieved during CPR preconditions the heart for the defibrillating shock. Despite the importance of CPR, it is often not performed in the field for a variety of reasons.

Cardiac electrotherapy stimuli having an amplitude that is greater than that of pacing-type stimuli, but less than the amplitude and energy level associated with defibrillation-type stimuli, are known in the art as medium voltage therapy (MVT). For example, U.S. Pat. No. 5,314,448 describes delivering low-energy pre-treatment pulses followed by high-energy defibrillation pulses, utilizing a common set of electrodes for both types of stimuli. According to one therapeutic mechanism of this pre-treatment, the MVT pulses re-organize the electrical activity within the cardiac cells of the patient to facilitate a greater probability of successful defibrillation with a follow-on defibrillation pulse. U.S. Pat. No. 6,760,621 describes the use of MVT as pretreatment to defibrillation that is directed to reducing the likelihood of pulseless electrical activity and electromechanical dissociation conditions as a result of the defibrillation treatment. The mechanism by which these results are achieved by MVT has been described as a form of sympathetic stimulation of the heart. These approaches are directed to influencing the electrochemical dynamics or responsiveness of the heart tissues.

MVT has also been recognized as a way of forcing some amount of cardiac output by electrically stimulating the heart directly with stimuli that cause the heart and skeletal muscles to expand and contract in a controlled manner. See U.S. Pat. Nos. 5,735,876, 5,782,883 and 5,871,510. These patents describe implantable devices having combined defibrillation, and MVT capability for forcing cardiac output. U.S. Pat. No. 6,314,319 describes internal and external systems and associated methods of utilizing MVT to achieve a hemodynamic effect in the heart as part of an implantable cardioverter defibrillator (ICD) for purposes of achieving a smaller prophylactic device. The approach described in the '319 patent uses the MVT therapy to provide a smaller and less expensive implantable device that can maintain some cardiac output without necessarily providing defibrillation therapy.

Unlike a conventional defibrillator or an IPG, which operates with the primary purpose of restoring a normal cardiac rhythm, MVT stimulation can be used to provide cardiac output, which in turn causes perfusion to the heart and brain, as well as other critical body tissues. By providing perfusion to the heart and other vital organs, MVT prolongs the life of the patient even while the patient continues experiencing the arrhythmia. Additionally, MVT improves the likelihood of successful defibrillation or of a spontaneous return of circulation. In another application, MVT may be utilized to place a heart into a distended state by continuing venous return in the absence of cardiac output, thus making it more likely to return to a spontaneous pulsatile rhythm. An AED equipped with MVT can provide consistent high quality chest compressions. In the case of an implanted ICD or IPG, back up chest compressions provided by MVT can, in one sense, be even more important than in an external, since in the case of the implantable device there may be no rescuer available to perform CPR when needed.

Recent studies have identified an increasing incidence of patients whose initial rhythm is not VF, but may be (PEA), or asystole. In addition in many cases an unsuccessful defibrillation shock (whether from an AED or an ICD) results in PEA, asystole or persistent VF. In all these cases the indicated therapy is CPR type chest compressions. Conventional ICD, IPG, and AED devices, even those enabled with MVT, work very well to treat VF, but provide little or no therapy for other common arrhythmias of cardiac arrest, namely, pulseless electrical activity (PEA) and asystole.

While developments in defibrillator technology, both automatic external defibrillators (AEDs) and implantable cardioverter defibrillators (ICDs) have made great strides in aiding the electrical cardiac resuscitation of individuals experiencing cardiac arrest, a need exists for a solution that can effectively treat the increasing number of victims that either present with non-VF cardiac arrest or are shocked into a non-VF non-pulsatile rhythm such as PEA or asystole.

U.S. Patent Application Publication No. 2006/0142809, currently pending, describes a technique and associated apparatus that combines defibrillation therapy with MVT into an external device having a capability to perform electrical CPR. Externally-applied MVT is proposed for stimulating skeletal and sympathetic muscles in addition to myocardial muscle tissue to effect chest compression and even ventilation in the patient. The '809 publication reflects the knowledge in the art that due to the inclusion of differing time constant components in an MVT waveform, the waveform can stimulate contraction of a variety of different types of muscles, e.g., myocardial, skeletal, sympathetic muscles, and the phrenic nerve. Varying and controlling the MVT waveform parameters, including variation of the musculature targeted by the waveform, is described as a way to maximize coronary perfusion pressure generated by application of MVT.

Notwithstanding the advancements in MVT for cardiac output forcing made to-date, known MVT techniques have been shown to be effective for only a limited time due to muscle fatigue resulting from application of the MVT. Particularly, after repeated application of the MVT electrical pulses, the muscles being stimulated become unresponsive to further MVT stimulation, resulting in a drop-off in coronary perfusion. A solution is therefore needed for enabling longer duration and more productive MVT sessions.

SUMMARY OF THE INVENTION

One aspect of the invention is directed to advanced monitoring and control of medium voltage therapy (MVT) in implantable and external devices. Apparatus and methods are disclosed that facilitate dynamic adjustment of MVT parameter values in response to new and changing circumstances such as the patient's condition before, during, and after administration of MVT. MVT is selectively targeted to specific muscles using variation of waveform characteristics, and/or using specific location-based targeting. The MVT is applied and adjusted based on monitored patient condition information, including monitored hemodynamic information. Administration of MVT is automatically and dynamically adjusted to achieve specific treatment or life-support objectives. One such objective is prolongation of the body's ability to endure and respond to MVT. Other objectives are specific to the type of arrhythmia or other pathologic state of the patient.

In another aspect, advanced monitoring techniques are applied to detect and treat specific conditions, such as pulseless electrical activity (PEA), for example. In one type of embodiment, MVT treatment electrodes are utilized to make hemodynamic measurements. In one particular example, hemodynamic measurements are made concurrently with the administration of the MVT. In another type of embodiment, the administration of MVT is controlled such that the MVT is synchronized with the ECG of a PEA condition.

In another aspect, methods and apparatus are described for administering a multi-tier MVT treatment algorithm, to be carried out by an implantable or external MVT-enabled device. The device according to one embodiment is configured to apply a higher intensity MVT at certain stages of rescue or life support, and to apply a lower intensity MVT at other stages. The intensity of MVT is varied by adjusting certain MVT parameters in response to a monitored condition of the patient. Higher-intensity and lower-intensity MVT may be selectively applied differently between MVT targeting the heart and MVT targeting the skeletal muscles, depending on the treatment objective, which in turn depends on the detected patient condition obtained using the patient monitoring facilities of the device.

In another aspect of the invention, adaptive MVT is applied to support patients in non life-critical conditions but where the heart may benefit from a certain level of assistance, such as orthostatic hypotension, for example. Hemodynamic monitoring and ECG measurements are used to identify such conditions, and to control proper administration of the MVT.

A number of advantages will become apparent from the following Detailed Description of the Preferred Embodiments.

BRIEF DESCRIPTION OF THE DRAWINGS

The invention may be more completely understood in consideration of the following detailed description of various embodiments of the invention in connection with the accompanying drawings, in which:

FIG. 3C is a diagram illustrating various examples of electrodes and sensors of the patient interface of the device of FIG. 3A.

Figure 1:
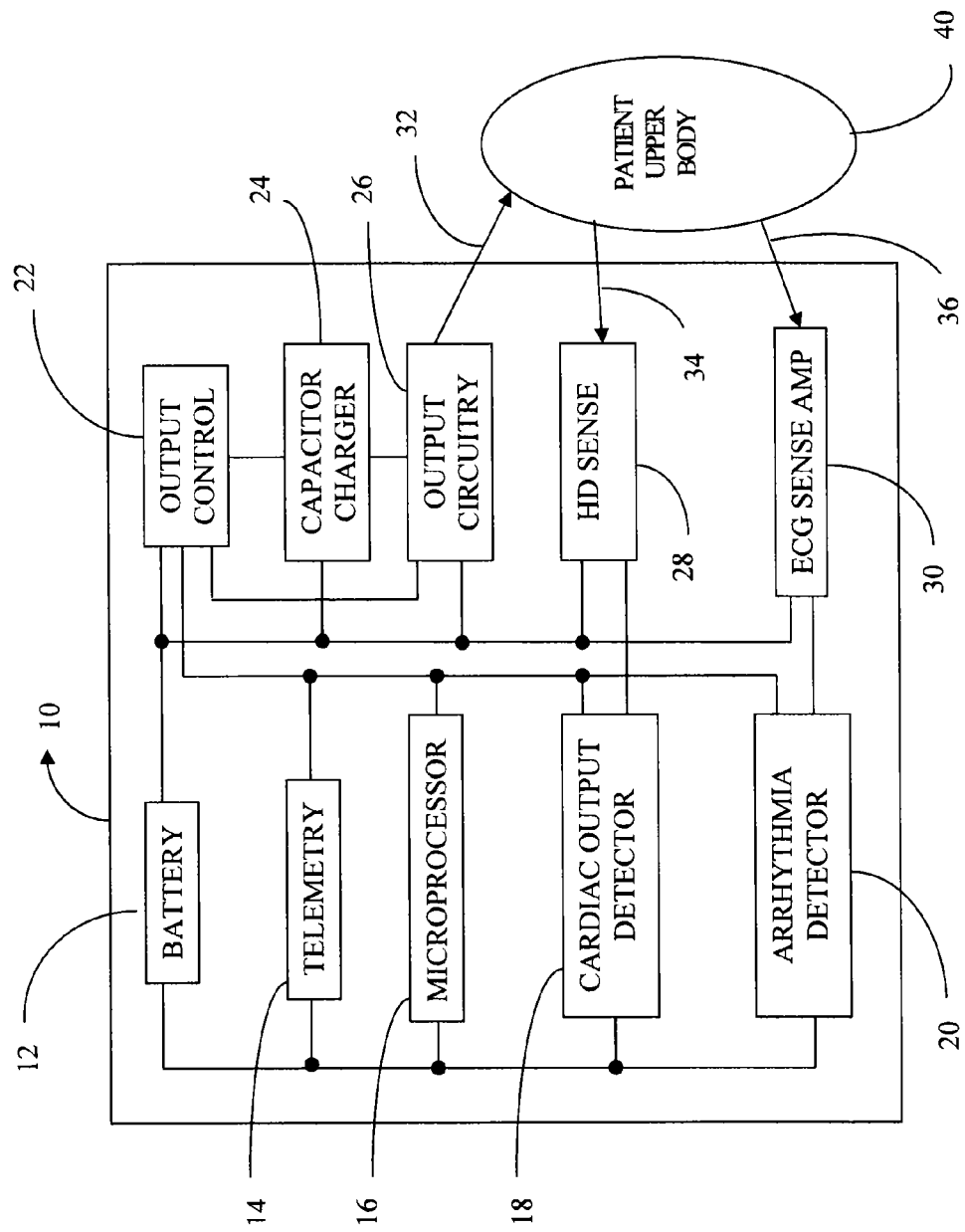
FIG. 1 is a diagram illustrating the sub-systems of an implantable device enabled with medium voltage therapy (MVT) facilities, according to one embodiment.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE PREFERRED EMBODIMENTS

FIG. 1 is a block diagram illustrating an implantable MVT device 10 constructed in accordance with one aspect of the invention. The device circuitry is electrically coupled with regions of the patient's upper body 40 via a series of leads— output lead 32, pressure sense lead 34, and ECG sense lead 36. The electronic circuit includes a conventional ECG amplifier 30 for amplifying cardiac signals. The amplified cardiac signals are analyzed by a conventional arrhythmia detector 20 which determines if an arrhythmia is present. The arrhythmia detector 20 may be one of several types well known to those skilled in the art and is preferably able to distinguish between different types of arrhythmias. For example; fibrillation, tachycardia, asystole.

The exemplary circuit also contains a hemodynamic sensing section 28 which amplifies and conditions a signal from a one or more hemodynamic sensors such as, for example, a pressure sensor within the heart or artery, such as the pressure sensor described in U.S. Pat. No. 6,171,252, the disclosure of which is incorporated by reference herein. Another type of hemodynamic sensor that can be used in an implantable embodiment is a microphone and associated processing device for monitoring audible body sounds (much like an indwelling stethoscope) indicative of blood flow as described in U.S. Pat. No. 7,035,684, the disclosure of which is incorporated by reference herein. Yet another suitable hemodynamic sensing technique is one featuring an ultrasonic blood flow sensor, such as he Doppler pulse sensor described in U.S. Pat. No. 4,823,800, the disclosure of which is incorporated by reference herein. Still another hemodynamic sensing technique that may be employed is impedance plethysmography (tomography) in which a series of electrodes are placed to measure changing impedance in localized regions indicative of blood flow, a pulse, or movement of the cardiac wall such as described in U.S. Pat. No. 5,824,029, the disclosure of which is incorporated by reference herein. A further technique of measuring the hemodynamic output of the patient is with the use of a pulse oximeter such as the implantable one described in U.S. Pat. No. 4,623,248, the disclosure of which is incorporated by reference herein.

The output of the hemodynamic sense circuit 28 is fed to a cardiac output detection circuit 18 which analyzes the data and determines an estimate of the cardiac output. Data from the arrhythmia detector circuit 20 and the cardiac output detection circuit 18 is fed to the microprocessor 16. The microprocessor 16 determines if MVT is appropriate, and what MVT parameters to apply at the present time. If MVT is indicated, the microprocessor 16 prompts the output control 22 to charge a capacitor within the output circuit 26 via the capacitor charger 24. The output control 22 directs the output circuitry 26 to deliver the pulses to the patient's upper body regions 40 via the output leads 32. The microprocessor 16 may communicate with external sources via a telemetry circuit 14 within the device 10. The power for the device 10 is supplied by an internal battery 12.

Figure 2A:
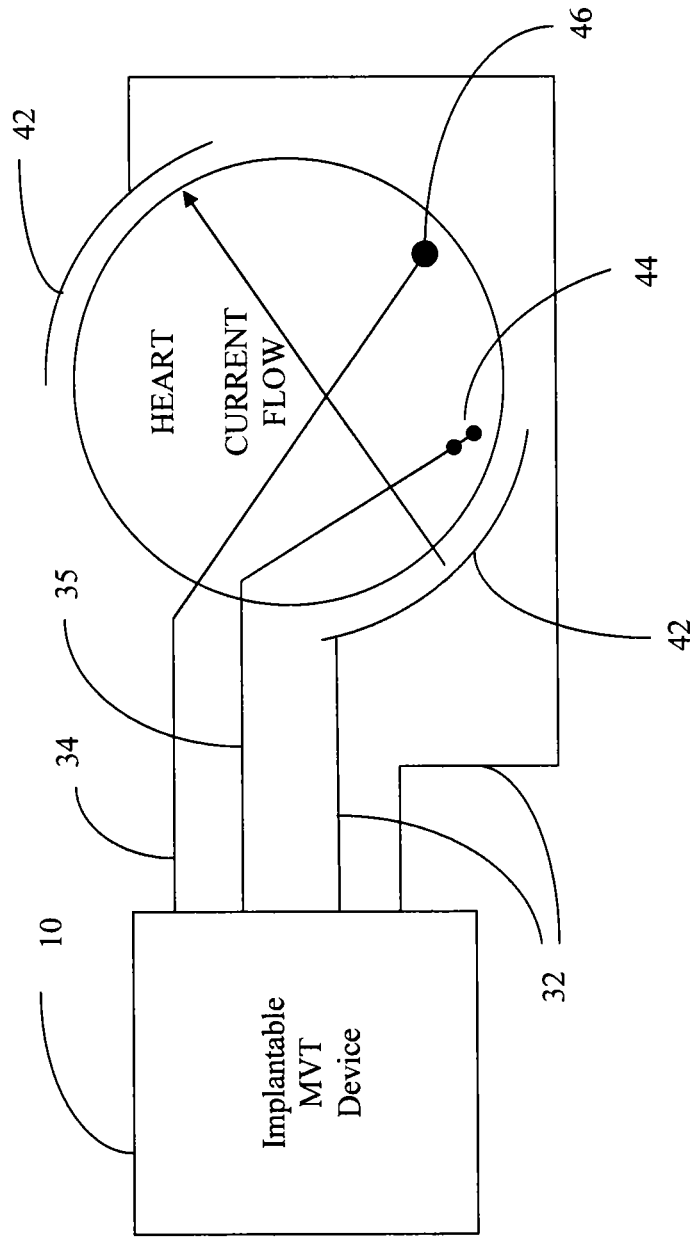
FIGS. 2A-2C illustrate various examples of electrode arrangements for implantable MVT devices such as the device of FIG. 1 according to various embodiments.

FIG. 2A is a diagram showing the connection of an implantable device 10' according to one embodiment to the heart as one of the regions in the patient's upper body 40 in an epicardial patch configuration. In this thoracotomy configuration, current passes through an output lead pair 32 to electrode patches 42 which direct the current through the heart. A pressure sense lead 34 passes the signal from an optional pressure transducer 46 which lies in the heart. The ECG is monitored by sense electrodes 44 and passed to the device 10' by a lead 36. The area of the electrodes 42 is at least 0.5 cm². The size of the electrode is greater than that of a pacing lead and no more than that of a defibrillation electrode or between approximately 0.5 cm² and 20 cm² each.

Figure 2B:
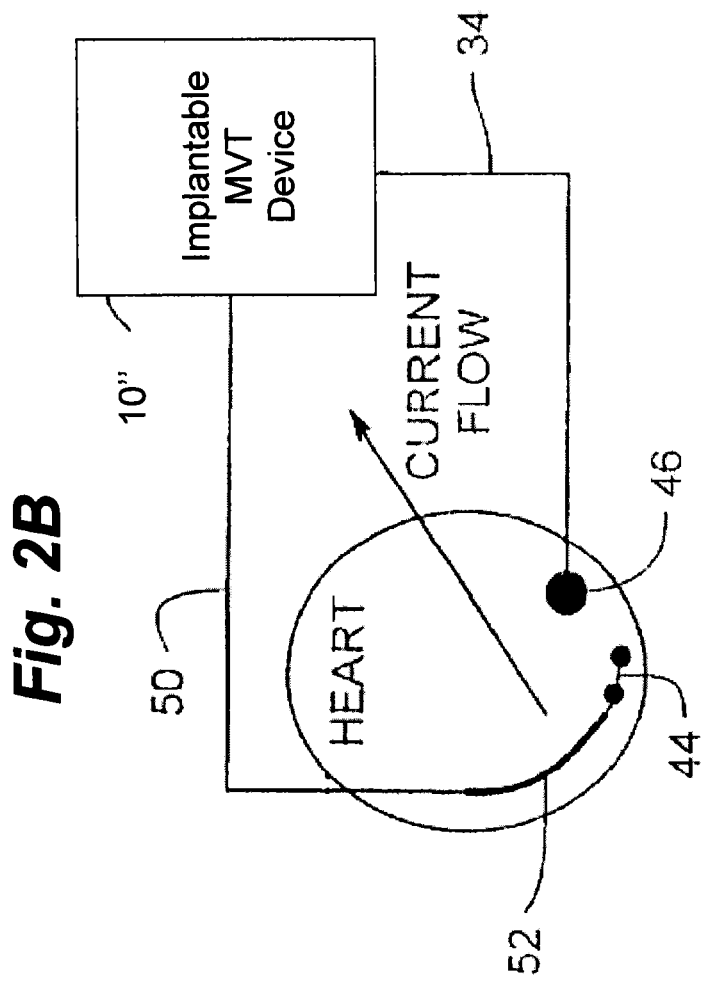

FIG. 2B illustrates an example of a non-thoracotomy arrangement according to one embodiment. In this system, the current passes from a coil electrode 52 in the heart to the housing of the MVT device 10". An endocardial lead 50 combines the ECG sensing lead and the pulse output lead. The ECG is monitored by sense electrodes 44 in the heart and passes through the endocardial lead 50. There is an optional pressure transducer 46 in the heart which passes a signal to the device 10" via optional lead 34.

Figure 2C:
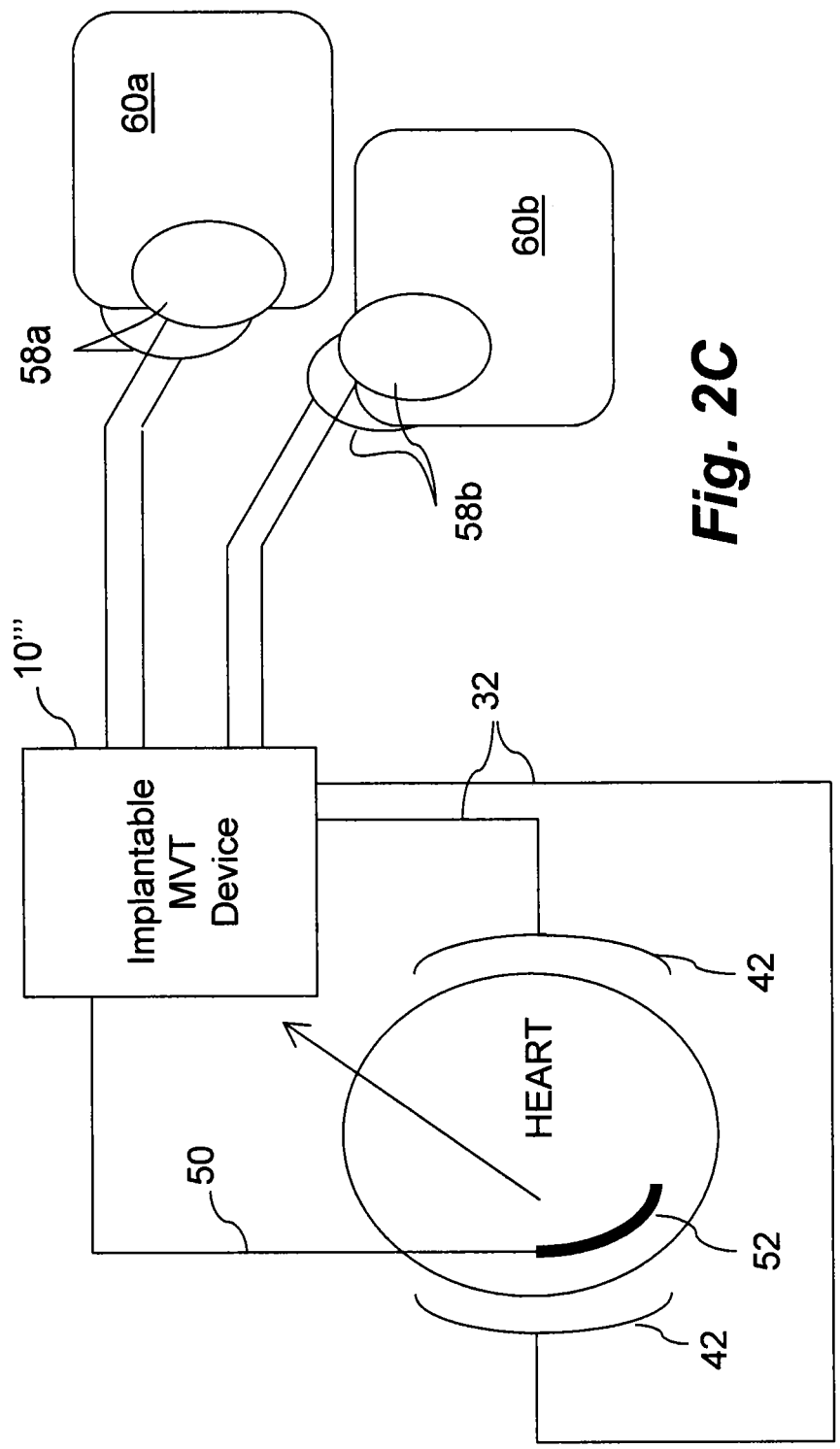

FIG. 2C illustrates an implantable MVT device 10''' that supports a set of diverse electrode arrangements for selectively applying MVT to different areas of the patient. In addition to electrodes 42 and 52 discussed above in the thoracotomy and non-thoracotomy arrangements for directing the MVT through the myocardium, device 10''' further includes additional electrodes 58a and 58b for placement at specific locations in the patient's upper body, 60a and 60b, to direct MVT through non-cardiac muscles. Examples of locations 60a and 60b include (without limitation) locations for activating the pectorial muscles, intercostals muscles, the diaphragm (e.g., via stimulation of the phrenic nerve), and the abdominal muscles. The additional electrodes 58a and 58b, in various embodiments, have a variety of constructions and locations, including, for example, subcutaneous patch electrodes, one or more additional electronics/battery housings, intra-vascular leads, and the like. Placements include any suitable location such as, for example, subcutaneously at the base of the neck, in the azygos vein, in the cephalic vein, subcutaneously in the lower torso, and subcutaneously on one or both sides of the upper torso.

In a related embodiment, the additional one or more of electrodes 58a and 58b are used for hemodynamic measurements such as, for example, electrical impedance plethysmography or tomography. In one such embodiment, one of the additional electrodes 58a, for instance, is implanted high in the upper chest region or at the base of the neck, while another one of the additional electrodes, 59a, for instance, is implanted lower in the abdominal region. Even though electrode 58a and electrode 59a may not used as a cathode/anode pair for application of MVT (this would be the case where, for example, electrode 58a has a complementary electrode 58a placed elsewhere for applying MVT to region 60a, and where electrode 59a has a complementary electrode 59a placed elsewhere for applying MVT to region 60b), one of electrodes 58a and one of electrodes 59a can be operated as an anode/cathode pair with each other for purposes of impedance measurement to determine blood flow, using a suitable switching arrangement in the implantable MVT device 10'''.

In a related embodiment, an electrical impedance measurement is performed using frequency division or code division multiplexing relative to applied MVT therapy. Thus, the impedance measurement may be carried out while rejecting the interference caused by application of the MVT signals. This approach permits a hemodynamic impedance measurement to be performed without having to interrupt application of the MVT and without having to time the measurement to coincide with time periods between MVT pulse packets. Accordingly, in one embodiment, a real-time, continuous hemodynamic monitoring is performed while MVT is administered. The blood flow can thus be plotted as a function of time, and correlated to the parameters of the MVT being applied. This information can be displayed to an operator as a chart recording or displayed trace, and can be automatically stored and analyzed to ascertain MVT performance.

Figure 3A:
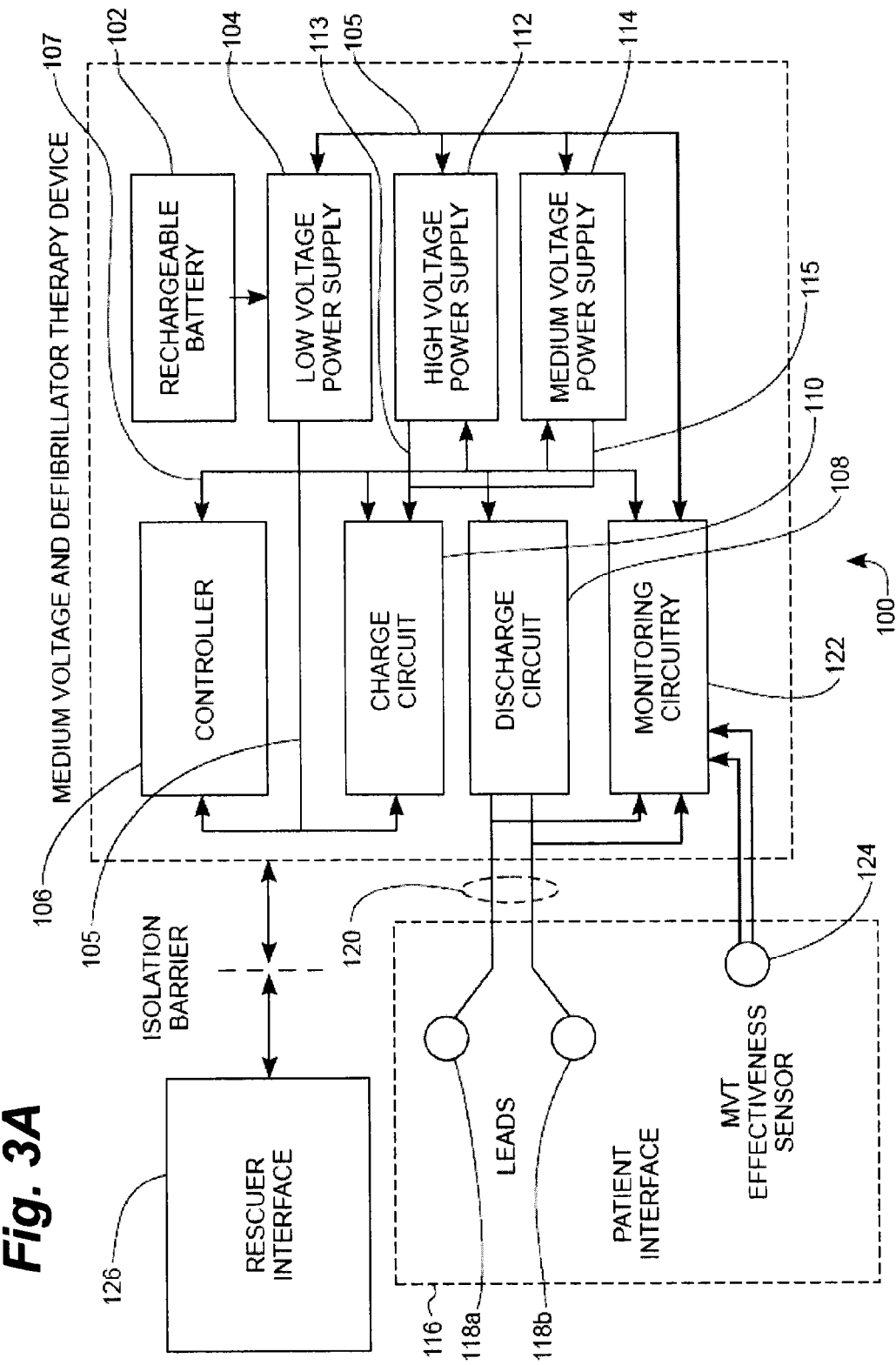
FIG. 3A is a diagram illustrating the sub-systems of an external device enabled with medium voltage therapy facilities, according to one embodiment.

FIG. 3A is a diagram illustrating an example AED 100 that utilizes MVT according to one embodiment. AED 100 can be a hand-portable instrument that is self-powered from an optionally-rechargeable battery 102. Battery 102 provides an energy source that can be converted and conditioned for powering the various circuitry of AED 100. A low voltage power supply 104 converts the battery power into one or more stabilized power supply outputs 105 for supplying the power to the subsystems of AED 100. The subsystems include a controller 106, for example a microprocessor that is programmed and interfaced with other subsystems to control most of the functionality of AED 100.

In the embodiments in which the controller 106 is implemented as a microprocessor or microcontroller, the microprocessor interface includes data and address busses, optional analog and/or digital inputs, and optional control inputs/outputs, collectively indicated at microprocessor interface 107. In one example embodiment, the microprocessor is programmed to control the sequence of the electrotherapy, as well as the output waveform parameters. The user input to the system can be in the form of simple pushbutton commands, or voice commands.

Example AED 100 includes a discharge circuit 108 for administering therapeutic stimuli to the patient. Discharge circuit 108 controls the release of therapeutic energy to achieve a desired stimulus having a particular waveform and energy. Charge circuit 110 energizes discharge circuit 108 to achieve the desired output stimulus. High voltage power supply 112 provides a sufficient energy source 113 to charge circuit 110 to enable charge circuit 110 and discharge circuit 108 to ultimately deliver one or more defibrillation pulses to an exterior surface of the patient. Typically, a voltage sufficient to achieve a therapeutic defibrillation stimulus from the exterior of a patient is in the range of 1 kV-3 kV.

In accordance with this embodiment, AED 100 also includes a medium voltage power supply 114. Medium voltage power supply 114 provides a medium voltage source 115 that enables charge circuit 110 and discharge circuit 108 to ultimately deliver one or more MVT signals to the exterior of the patient. In one embodiment, the medium voltage power supply is adapted to provide a regulated voltage in the range from 20-1000 V.

The defibrillation and MVT stimuli are administered to the patient via patient interface 116. In one embodiment, patient interface 116 includes electrodes 118a and 118b that are adhesively applied to the patient's chest area, typically with an electrically-conductive gel. Electrodes 118a and 118b are electrically coupled, such as by insulated copper wire leads 120, to discharge circuit 108. In one example embodiment, electrodes 118a and 118b can deliver the defibrillation stimuli and the MVT stimuli as well as obtain information about the patient's condition. For example, electrodes 118 can be used to monitor the patient's cardiac rhythm. Signals originating in the patient that are measured by electrodes 118 are fed to monitoring circuitry 122.

In one embodiment, electrodes 118a and 118b are part of compound electrode patches in which each patch (having a common substrate) has a plurality of individually-selectable electrodes. In this arrangement, device 100 is programmed to select certain ones of the individual electrodes on each compound patch to achieve a therapeutic purpose. One such purpose is to activate an individual electrode that is most optimally placed on the patient's body for the desired MVT or defibrillation therapy. This approach can be used to correct for the variability in placement of the electrode patches by unskilled rescuers or even skilled rescuers working under difficult circumstances in the field. Device 100 in this embodiment may include a switching arrangement, either electromechanical or electronic, or may communicate control information to an external switching arrangement, which may be incorporated into the compound patch. In a related embodiment, the ECG signal strength, as measured using various pairs of the individual electrodes of the compound patches, is used to determine the electrodes to be used for MVT and/or defibrillation administration. In another related embodiment, the hemodynamic measurement of the MVT effectiveness, as recorded for different electrode pairs, is used as a basis for switchably selecting the electrodes to be used for defibrillation. In yet another embodiment, certain electrodes are selected from among the plurality of electrodes on each compound patch to target specific regions to which MVT is to be applied.

In one embodiment, patient interface 116 includes an MVT effectiveness sensor 124 coupled to monitoring circuitry 122. MVT effectiveness sensor 124 can measure observable patient characteristics that are related to the patient's condition, in like fashion to the hemodynamic monitoring and determining arrangements described above for an implantable embodiment. Additional details about the MVT effectiveness monitoring are discussed below.

AED 100 also includes a rescuer interface 126 operatively coupled with controller 106. In one embodiment, rescuer interface 126 includes at least one pushbutton, and a display device for indicating at least the operational status of AED 100. In a related embodiment, rescuer interface includes a system for providing visual or audible prompting or instructions to the rescuer. In another embodiment, rescuer interface 126 includes a plurality of human-operable controls for adjusting the various AED operational parameters, and a display device that indicates measurements made by monitoring circuitry 122.

Figure 3B:
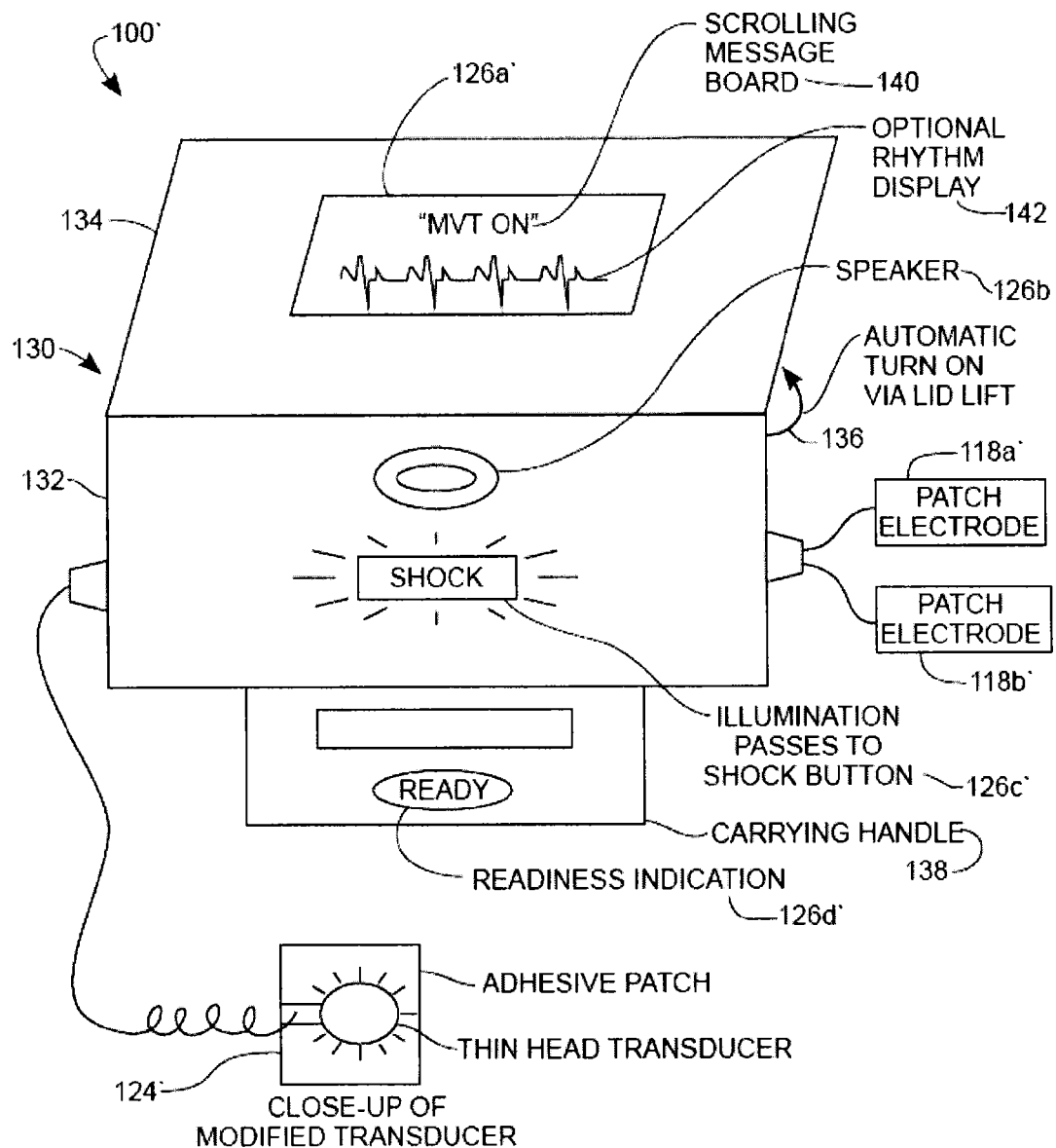
FIG. 3B is a diagram illustrating an exemplary operator interface of the device of FIG. 3A.

FIG. 3B is a diagram illustrating human interface portions of example AED 100' according to one embodiment. AED 100' is a physical implementation of AED 100 (FIG. 1A). AED 100' is housed in a lightweight portable housing 130 having a base portion 132 and a hinged lid 134 in an exemplary clam-shell arrangement as illustrated, where opening and closing of the lid turns the device on and off, as diagrammed at 136. Other embodiments do not have the base-cover arrangement, and instead have a housing consisting of a single enclosure, in which case the device has an on/off switch. The device's relatively small size and weight, and carrying handle 138 facilitate hand-portability of the device. Display 126a' may have a text only display 140 or may include a graphical display 142 that could, among other items, display an ECG waveform. The device also has a speaker 126b for voice prompting of the proper rescue sequence, a non-volatile readiness indicator 126d' that indicates whether or not the device is in working order, an optional "shock" button 126c' and receptacles for the patient electrodes 118a' and 118b' and an MVT effectiveness sensor 124'.

AED 100' includes two types of patient interface. First, electrodes 118a' and 118b' are adapted to be adhesively coupled to the patient's skin. In one embodiment, the adhesive consists of an electrically conductive gel. Electrodes 118a' and 118b' can be used to measure the patient's cardiac rhythm, and to apply MVT and defibrillation therapy to the patient. Second, MVT effectiveness sensor 124' includes a transducer adapted for measuring one or more vital signs of the patient.

FIG. 3C is a diagram of several possible patient 160 connections to an AED 158 according to one embodiment including: defibrillation/ECG electrodes 118a' and 118b', pulse oximeter 124a', ETCO2 sensor 124b', Doppler or ultrasound pulse sensor 124c', and blood pressure sensor 124d'. More generally, the MVT Effectiveness sensor can be a variant of any of the monitoring techniques discussed above, for instance, the pulse oximetry measurement for an external embodiment may be achieved using a fingertip pulse oximeter as the MVT effectiveness sensor 124. Other suitable techniques for monitoring a hemodynamic state of the patient may also be used. For instance, alternatively or in conjunction: a pulse oximeter, a sonic arterial pulse sensor, a gas sensor, or a blood pressure sensor. In another embodiment, the $O_2$ saturation sensor 124a', end tidal sensor 124b', and pulse detection unit 124c', are battery-powered and are adapted to communicate measurement data via wireless radio frequency link. For example, Bluetooth technology could be utilized to accomplish close-range wireless data communications.

In one example embodiment, arterial pulse activity measured from an exterior of the patient by way of pressure sensing, or by way of Doppler ultrasound technology. In one embodiment, the MVT effectiveness sensor includes a transthoracic impedance measuring arrangement that detects changes in the chest impedance with cardiac output. Referring again to FIG. 3B, in one embodiment, MVT effectiveness sensor 124' is integrated with an adhesive patch adapted to be attached to the patient's skin. In a related embodiment, the transducer portion of MVT effectiveness sensor 124' is implemented in a thin-or-thick-film semiconductor technology. Examples of suitable sites for arterial pulse sensing include the patient's aorta, femoral arteries, carotid arteries, and brachial arteries. Other accessible arteries may also be suitable. In one example embodiment of AED 100', the measurement collected via MVT effectiveness sensor 124' is displayed, substantially in real-time, on display 126'. The displayed measurement can be numerical or graphical, such as a bar-type or chart recorder-type display.

In a related embodiment, a plurality of different techniques may be used together in a more advanced AED device enabled with MVT. Such devices, with their multiple sensors to engage with the patient, may be more suitable for use by trained rescuers, such as paramedics, for example.

In operation, AED 100 is interfaced with the patient via leads 118a/118b, and MVT effectiveness sensor. In one embodiment, AED 100 provides guidance to a rescuer, via rescuer interface 126, for properly interfacing with the patient. AED 100 measures the patient's condition using monitoring circuitry 122 and at least a portion of the patient interface 116. Next, AED 100 analyzes the measured patient's condition to determine the existence of any indications for treating the patient. If the patient exhibits a condition treatable by AED 100, the device determines the type of therapeutic signal to apply to the patient, and proceeds to apply the treatment. The therapeutic signal can be an MVT signal, CPR prompt, or a defibrillation signal, either of which is delivered via discharge circuit 108 and leads 118a/118b. During a rescue process, AED 100 provides prompting or instructions to a rescuer for facilitating the therapy and for protecting the rescuer's safety.

Speaking generally for both, implantable, and external MVT-equipped electrotherapy devices, in various embodiments, a plurality of different MVT waveforms adapted to force muscular contractions are disclosed herein. The waveforms are each adapted to repeatedly artificially force and maintain musculature of the patient in a contracted state for a time sufficient to achieve myocardial perfusion and to subsequently cause the musculature to relax, thereby achieving a forced hemodynamic effect sufficient to reduce a rate of degradation of the patient's physical condition resulting from a cardiac arrhythmia.

The MVT waveforms discussed herein are administered at a higher energy than a pacing pulse, but at a lower energy than a defibrillation pulse. A pacing pulse is adapted to initiate a myocardial cell activation process in the heart, wherein myocardial tissue naturally contracts due to the heart's natural activation wavefront propagation. Pacing merely adjusts natural cardiac activity, such as electrically stimulating cardiac muscles such that they contract synchronously across different regions of the heart. Therefore, a pacing waveform is incapable of electrically forcing and/or maintaining a heart contraction or inducing cardiac perfusion during a cardiac event such as ventricular fibrillation. A defibrillation pulse, on the other hand, involves the delivery of energy sufficient to shock the heart into a "reset state", and is intended to reset the natural electrical activity of the heart. In contrast with pacing and defibrillation pulses, in one embodiment, the MVT waveforms as discussed herein are delivered with sufficient energy to electrically force a cardiac contraction, however without delivering energy intended to perform a cardiac "reset" such as would result from a defibrillation pulse. In various embodiments, the MVT waveforms discussed herein adapted to artificially force and maintain the heart in a contracted state for a time sufficient to achieve cardiac perfusion.

Figure 4A:
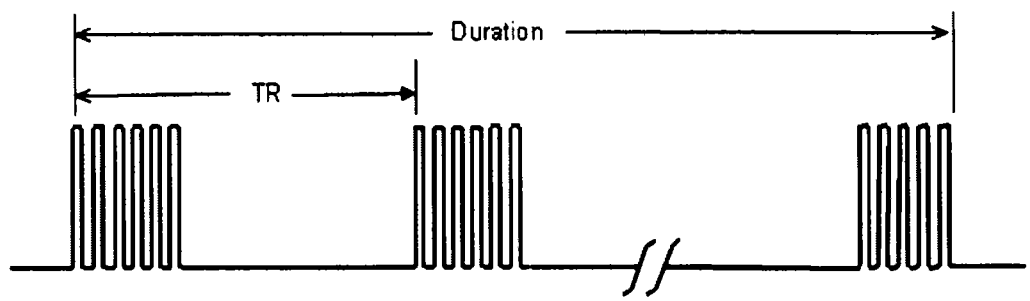
FIGS. 4A-4B are time-domain waveform diagrams illustrating variable parameters of the MVT according to various embodiments of the invention.
Figure 4B:
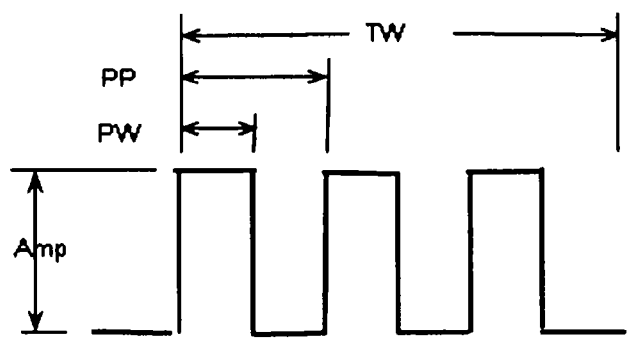

FIG. 4A is a diagram illustrating some of the general parameters of the MVT pulse waveforms The train rate TR can be considered to be the forced "heart rate" in beats per minute, since a pulse packet produces one chest constriction. The duration is the length of time for during which a single session of MVT is applied. FIG. 4B is a diagram detailing a single pulse packet, having parameters of amplitude (AMP), pulse width PW, pulse period PP, and train width TW.

Certain effective parameters have been reported in the following published manuscripts, incorporated by reference herein: "Transthoracic Application Of Electrical Cardiopulmonary Resuscitation For Treatment Of Cardiac Arrest," Crit Care Med, vol. 36, no. 11, pp. s458-66, 2008 and "Coronary Blood Flow Produced by Muscle Contractions Induced by Intracardiac Electrical CPR during Ventricular Fibrillation," PACE vol. 32, pp. S223-7, 2009.

Table 1 below provides an exemplary range of parameter values corresponding to empirically determined effectiveness.

TABLE 1

Exemplary Parameter Value Ranges for MVT

| Parameter | Value of Parameter (Implanted Devices) | Value of Parameter (External Devices) |
| --- | --- | --- |
| MVT Duration | 20-120 sec. | 20-120 sec. |
| Train Rate | 30-120 per min. | 30-120 per min. |
| Pulse Current Amplitude | 0.25-5 A | 0.25-5 A |
| Pulse Voltage Amplitude | 15-250 V | 60-300 V |
| Pulse Width | 0.15-10 ms | 0.15-10 ms |
| Pulse Period | 5-70 ms | 5-70 ms |

In a related aspect of the invention, the MVT waveform is tuned to increase selectivity of muscle type in the application of the MVT. Muscle type selectivity permits more precise targeted treatment based on the patient's condition, and facilitates management of muscle fatigue to prolong the MVT treatment duration.

An MVT waveform that is optimized for skeletal muscle capture (OSC) according to one embodiment is adapted to force primarily skeletal muscle contractions. The OSC waveform is adapted to force a contraction and subsequent release of skeletal muscles in order to achieve perfusion of the heart and other vital organs, and can force some amount of ventilation.

An MVT waveform that is optimized for myocardial capture (OMC) according to a related embodiment is adapted to force cardiac muscle contractions. The OMC waveform is adapted to force contraction of primarily cardiac muscles in order to achieve some level of perfusion for the heart and other vital organs. Tables 2 and 3 below provide exemplary ranges for OSC and OMC MVT parameter values; whereas tables 4 and 5 below provide an exemplary optimal set of values for OSC and OMC waveforms, respectively.

TABLE 2

Example Ranges of Optimal OSC Parameter Values.

| Variable Parameter | Optimal Range |
| --- | --- |
| Pulsed Output Voltage | 75-300 V (external); 20-80 V (implantable) |
| Pulsed Output Current | 1-5 A |
| Pulse Width | .10-.25 ms |
| Pulse Period | 10-20 ms |
| Duration | 10-30 seconds |
| Packet Width | 100-300 ms |
| Train Rate | 80-160 bpm |

TABLE 3

Example Ranges of Optimal OMC Parameter Values.

| Variable Parameter | Optimal Range |
| --- | --- |
| Pulsed Output Voltage | 75-300 V (external); 20-80 V (implantable) |
| Pulsed Output Current | 1-5 A |
| Pulse Width | 5-10 ms |
| Pulse Period | 20-40 ms |
| Duration | 10-30 seconds |
| Packet Width | 100-300 ms |
| Train Rate | 80-160 bpm |

TABLE 4

Exemplary Stimulation Waveform for OMC

| Variable Parameter | Optimal Value |
| --- | --- |
| Pulsed Output Voltage | 75-300 V (external); 20-80 V (implantable) |
| Pulsed Output Current | 2 A |
| Pulse Width | 7.5 ms |
| Pulse Period | 30 ms |
| Duration | 20 seconds |
| Packet Width | 200 ms |
| Train Rate | 120 bpm |

TABLE 5

Exemplary Stimulation Waveform for OSC

| Variable Parameter | Optimal Value |
| --- | --- |
| Pulsed Output Voltage | 75-300 V (external); 20-80 V (implantable) |
| Pulsed Output Current | 2 A |
| Pulse Width | .15 ms |
| Pulse Period | 15 ms |
| Duration | 20 seconds |
| Packet Width | 200 ms |
| Train Rate | 120 bpm |

In one type of embodiment, the waveform parameters are varied or modulated for different purposes. One such purpose is to enhance or adjust the MVT effectiveness—that is, to vary the hemodynamic and other electrostimulation effects to achieve one or more treatment goals. One such treatment goal is management of muscle fatigue. MVT stimulation can, in a matter of a few minutes, fatigue the heart or other muscles to a point where they become un-responsive to further stimulation. Accordingly, in this embodiment, the MVT parameters are set or adjusted to minimize, or simply reduce, MVT-induced muscle fatigue, thereby allowing the MVT treatment to be prolonged.

In one example embodiment, the MVT-enabled implantable or external electrotherapy device uses its hemodynamic monitoring facilities to measure variables such as blood flow, blood pressure, or blood oxygenation, or a combination thereof. Using this measured information, the intensity and targeting of the MVT is adjusted. To illustrate targeting, in one specific example, when the monitored hemodynamic output from MVT stimulating the heart with an OMC waveform begins to decrease, the MVT circuit responds to the reduction by switching to a OSC waveform to stimulate the non-cardiac muscles and give the heart the opportunity to rest and either conserve or restore its ATP stores. To illustrate adjustment of MVT intensity, the pulse amplitude, or pulse period (or both) are adjusted to reduce the degree of stimulation being applied while the hemodynamic condition is monitored. In one situation, the MVT intensity is reduced to a minimum level where the hemodynamic output is still adequate. This reduction in intensity reduces muscle fatigue effects and preserves battery life of the device, which also prolongs the MVT treatment duration that is possible.

In a related example, for a device that performs defibrillation therapy, the controller is programmed to adjust the MVT parameters to improve the likelihood of successful defibrillation. Accordingly, in this embodiment, as the time to administer the defibrillation shock approaches, the MVT-enabled defibrillator switches to the OSC waveform for stimulating primarily non-cardiac muscles. This gives the heart more time to rest, and to be in a "fresher" state for receiving the defibrillation therapy, which improves the likelihood of successful conversion of the arrhythmia with defibrillation.

In another embodiment, for either the OSC, or OMC waveforms, or in another type of MVT waveform which may be non-targeted to muscle groups, the pulse period is modulated during administration of the MVT administration. The degree of modulation can be in the neighborhoods of 5%, 10%, 15%, or more. In one variant of this embodiment, the modulation is randomized, or noise-like. In another embodiment, the modulation is applied with a certain pattern (i.e., with a predetermined modulating signal), or with a certain combination of patterns, which can be alternated based on randomization or based on one or more alternation functions. Modulation of the pulse period in any of these fashions may help to recruit more muscle fibers than a MVT signal with non-modulated pulse period, and may reduce or delay the onset of muscle fatigue caused by MVT. Additionally, the modulation of pulse period may enhance the hemodynamic effect, which in turn permits a reduction in pulse amplitude for an equivalent hemodynamic output or sympathetic stimulation effect.

In a further aspect of the invention, the various electrodes described above for MVT administration can be selectively switched in and out of the pulse generating circuitry, enabling selective application of MVT to specific regions of the body (corresponding to specific muscles or muscle groups). Table 6 below lists various exemplary muscles that are individually targeted in one type of embodiment.

TABLE 6

Exemplary Muscles Targeted through Specific MVT Electrode Placement

| Muscle ID | Muscle Description |
| --- | --- |
| A | Heart |
| B | Right Pectoral |
| C | Left Pectoral |
| D | Right Intercostals |
| E | Left Intercostals |

TABLE 6-continued

Exemplary Muscles Targeted
through Specific MVT Electrode Placement

| Muscle ID | Muscle Description |
|---|---|
| F | Right Abdominals |
| G | Left Abdominals |

In one type of embodiment according to this aspect of the invention, the targeting of muscles is automatically coordinated and varied based on changing circumstances, by the MVT-enabled device, to achieve a desired therapeutic effect based on the monitored patient condition, including the type of arrhythmia, the hemodynamic effect of applied MVT, and on the specific treatment or rescue algorithm being administered. In a related embodiment, the targeting of specific muscles is coordinated with the MVT waveform to be applied to further enhance the specificity of the MVT targeting.

One example of the desired therapeutic effect is management of muscle fatigue. In a corresponding embodiment, certain muscles are stimulated by MVT for longer or shorter durations based on that muscle's endurance of MVT. In a related embodiment, muscle groups having left and right sides, i.e., pectorals, intercostals, abdominals, are stimulated such that only one side at a time is activated by MVT, allowing the other side to rest and recuperate. Variation of muscle selection can be predetermined according to a programmed algorithm which is selected in response to the detected type of arrhythmia. Alternatively, to account for variation among patients, selection of muscles for stimulation is made in response to hemodynamic monitoring.

In one embodiment, the controller of the MVT circuit maintains a one or more data structures that relate the different muscles for which the device is configured to stimulate via MVT, to amplitude and waveform parameter information corresponding to that muscle group. In a related embodiment, the data structure(s) further include associations between treatment algorithms corresponding to various arrhythmias or patient conditions, as measured by the patient monitoring facilities of the device, and MVT parameter values to use for those arrhythmias or conditions.

In one example, the device is programmed to apply relatively higher intensity MVT to one type of muscle group (or one side of the body) than to another muscle group or side of the body as a test of endurance of the patient's musculature to MVT. The other side, which is less intensely stimulated, may then remain available for longer-duration MVT therapy.

In another embodiment, the device is configured with an algorithm to apply MVT as a test stimulus to assist in diagnosis of the patient's condition or in adjustment of the MVT parameters in order to provide better patient-specific treatment. In one example of such an embodiment, the hemodynamic monitoring includes both, blood flow information, and blood oxygenation information. MVT is applied to force perfusion and ventilation, and the hemodynamic condition is monitored. The presence of adequate blood flow being generated by the MVT, as measured by the blood flow monitoring, while the blood oxygenation reads lower than expected (based on baseline data stored in the device corresponding to the duration of the patient's arrhythmia and amount of flow measured), suggests that the patient is not achieving sufficient respiration. Accordingly, in this embodiment, the MVT is adapted to increase the proportion of time or degree of stimulation targeting muscles that provide a ventilation effect. Thus, for instance, the MVT may be adapted to stimulate the phrenic nerve for a longer period (to thereby cause the diaphragm to contract for a longer time, causing a larger breath to be forced).

In another example, hemodynamic monitoring is configured to distinguish between forced pulse output and return. In one particular embodiment, the device is configured to first test for a weak return, then test for a weak pulse. An indication of weak return but adequately high pulse pressure suggests that the heart is having difficulty expanding to fill with blood (e.g., tamponade). Accordingly, the MVT is automatically adapted to enhance and prolong the targeting of muscles that tend to expand the chest cavity, thereby lowering pressure around the heart to help draw in more blood. In another example, a strong return but weak pulse indicates that the heart is likely to have become distended. In response, the MVT is adapted to optimize contraction of the distended heart, such as, for instance, extending the duration of the pulse packets to force the heart to stay contracted for a longer period of time. Alternatively, or additionally, an OSC waveform can be synchronized with an OMC waveform such that one immediately follows the other. Thus, the heart can be compressed for an extended period by first capturing myocardial cells to contract, then by squeezing the heart using the skeletal muscles.

In yet another specific example of this aspect of the invention, hemodynamic monitoring is combined with ECG monitoring and MVT to identify and treat PEA. In this example, PEA is detected by the absence of hemodynamic output while the ECG measurement indicates the presence of a heart rhythm. In this condition, MVT is applied in synchronous fashion with the ECG. In one case, MVT is applied such that the forced contraction and permitted relaxation of the heart coincides with the QRS complex, thereby forcing the heart to beat as if the ECG and the mechanical action were normal. In another case, MVT is applied at a specific offset angle relative to the normal QRS complex and mechanical action. In a related case, the MVT is applied sequentially at a series of specific offset angles for each ECG cycle.

Another aspect of the invention is directed to a multi-tier MVT treatment algorithm, to be carried out by an implantable or external MVT-enabled device. The device according to one embodiment is configured to apply a higher intensity MVT at certain stages of rescue or life support, and to apply a lower intensity MVT at other stages. The intensity of MVT is varied by adjusting certain MVT parameters. For MVT waveforms targeting skeletal muscle, the pulse period is primarily varied to control the intensity of muscle contraction. For MVT waveforms targeting primarily the myocardium, the amplitude is the parameter primarily responsible for the MVT intensity. To a lesser extent, the pulse period may also be adjusted to control OMC intensity. Higher-intensity and lower-intensity MVT may be selectively applied differently between MVT targeting the heart and MVT targeting the skeletal muscles, depending on the treatment objective, which in turn depends on the detected patient condition obtained using the patient monitoring facilities of the device. Thus, for example, in certain circumstances, high-intensity MVT may be applied to skeletal muscles while low-intensity MVT is applied to the myocardium, and vice-versa.

In one embodiment, selection of high-intensity and low-intensity MVT is based in part on the duration of the arrhythmia, and on the current point in the treatment protocol. For example, in the case of a patient condition treatable with defibrillation or cardioversion, the MVT protocol requires high-intensity MVT prior to the shocks for converting the arrhythmia. More intensive MVT in this case places the heart in a better condition to respond favorably to the defibrillation or cardioversion. A refinement of this approach in a related embodiment distinguishes between MVT targeting the myocardium and MVT targeting skeletal muscles. In this refined approach, as discussed above, the myocardium is progressively given reducing-intensity MVT as the time to defibrillate approaches, while the skeletal MVT remains at a high-intensity. This improvement allows the heart to recover from the MVT. The reduced-intensity MVT applied to the heart may also be adjusted to optimize sympathetic stimulation (again, facilitating better defibrillation success) while reducing the MVT energy applied to force contraction, which fatigues the heart.

In a related embodiment, if defibrillation is unsuccessful following the standard protocol of 4-6 shocks, the MVT for both, the heart and the skeletal muscle, is automatically adjusted to their respective low-intensity modes so that the patient's life support can be prolonged with MVT. This becomes essentially a muscle fatigue management (and device energy conservation) strategy.

In another aspect of the invention, adaptive MVT is applied to support patients in non life-critical conditions but where the heart may benefit from a certain level of assistance. Hemodynamic monitoring and ECG measurements are used to identify such conditions, and to control proper administration of the MVT. In one such condition, orthostatic hypotension, an omni-directional accelerometer is included in the device, and is configured with the measuring circuitry and decision logic to detect blood pressure relative to movement and orientation of the patient. Thus, when the patient is standing up from a seated or reclined position, and when the patient's blood pressure fails to respond to accommodate such movement, MVT may be applied to assist the heart to develop more pressure. In one specific embodiment, the MVT for this application targets the myocardium, with a specific OMC waveform to reduce the discomfort the patient may experience due to inadvertent stimulation of skeletal muscle.

The embodiments above are intended to be illustrative and not limiting. Additional embodiments are within the claims. In addition, although aspects of the present invention have been described with reference to particular embodiments, those skilled in the art will recognize that changes can be made in form and detail without departing from the spirit and scope of the invention, as defined by the claims.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the present invention, it is expressly intended that the provisions of Section 112, sixth paragraph of 35 U.S.C. are not to be invoked unless the specific terms "means for" or "step for" are recited in a claim.

What is claimed is:

1. An electrotherapy device for treating arrhythmia in a patient, the device comprising:
   a patient interface including:
      a plurality of electrodes adapted to be placed in electrical contact with the patient; and
      at least one hemodynamic sensor;
   electrotherapy circuitry operatively coupled to the patient interface and including a medium voltage therapy (MVT) pulse generator adapted to supply the MVT via the patient interface as a configurable waveform having a set of adjustable waveform parameters, wherein the waveform is defined by series of pulse trains having an adjustable train repetition rate, the pulse trains being composed of pulses having an adjustable pulse width, an adjustable pulse period, and an adjustable pulse amplitude, the MVT being of an energy level insufficient to shock the heart into a reset state;
   patient monitoring circuitry including:
      arrhythmia monitoring circuitry operatively coupled to at least a pair of the plurality of electrodes; and
      cardiac output monitoring circuitry operatively coupled to the at least one hemodynamic sensor;
   a controller operatively coupled to the patient monitoring circuitry and the electrotherapy circuitry, and configured to:
      based on an output of the arrhythmia monitoring circuitry and on the cardiac output monitoring circuitry, ascertain a patient condition that is treatable by the MVT;
      based on a treatment or life-support objective corresponding to the patient condition treatable by the MVT, cause the electrotherapy circuitry to initiate application of the MVT to the musculature of the patient via the plurality of electrodes to target a selected muscle group, wherein the selected muscle group is repeatedly (a) forced into a contracted state, (b) maintained in the contracted state for a time sufficient to achieve myocardial perfusion, and (c) thereafter allowed to relax, thereby achieving a forced hemodynamic effect sufficient to reduce a rate of degradation of the condition of the patient;
      based on continued monitoring by the cardiac output monitoring circuitry during application of the MVT, adjust the waveform parameters in furtherance of the treatment or life-support objective such that:
         in response to a measured level of cardiac output during application of the MVT targeting a selected first muscle group exceeding a minimal level adequate for the treatment or life-support objective, reduce an intensity of MVT stimulation targeting the first muscle group;
         in response to a measured reduction of level of cardiac output during application of the MVT targeting a selected first muscle group, cause the electrotherapy circuitry to target a selected second muscle group distinct from the first muscle group with the MVT.

2. The electrotherapy device of claim 1, wherein the controller is configured such that the reduction in MVT intensity and targeting of the second muscle group are performed to reduce muscle fatigue in the first muscle group caused by the MVT.

3. The electrotherapy device of claim 1, wherein the first muscle group consists of primarily myocardial musculature and the second muscle group consists of primarily skeletal musculature.

4. The electrotherapy device of claim 1, wherein the first muscle group consists of primarily myocardial musculature and the second muscle group consists of primarily musculature of the diaphragm.

5. The electrotherapy device of claim 1, wherein the controller is configured to cause the electrotherapy circuitry to target the second muscle group by applying the MVT with a set of adjusted waveform parameters adapted to more efficiently stimulate to the second muscle group.

6. The electrotherapy device of claim 1, wherein the plurality of electrodes includes electrodes positioned at various regions of the torso of the patient, and wherein the electrotherapy circuitry is adapted to selectively apply the MVT to specific one or more regions via selected groupings of the plurality of electrodes such that various different muscle groups of skeletal musculature are selectively targeted, and wherein the first muscle group and the second muscle group respectively correspond to different regions of the torso of the patient.

7. The electrotherapy device of claim 6, wherein the controller maintains at least one more data structure that relates each of the different muscle groups to amplitude and waveform parameter information corresponding to that muscle group, wherein different muscle groups correspond to different waveform and amplitude characteristics.

8. The electrotherapy device of claim 6, wherein one of the muscle groups consists of skeletal muscles on the left side of the patient, and another one of the muscle groups consists of skeletal muscles on the right side of the patient.

9. The electrotherapy device of claim 6, wherein one of the muscle groups consists of abdominal muscles, and another one of the muscle groups consists of intercostals muscles.

10. The electrotherapy device of claim 1, wherein the electrotherapy circuitry further comprises:
a high voltage therapy (HVT) pulse generator operatively coupled to the patient interface and adapted to supply the HVT via the patient interface, wherein the HVT is of an energy level sufficient to shock the heart into a reset state; and
wherein the controller is further configured to:
based on a treatment or life-support objective corresponding to the patient condition treatable by the HVT, cause the electrotherapy circuitry to apply the MVT targeting primarily myocardial musculature at a progressively reducing intensity as a time at which the HVT is to be applied approaches;
cause the electrotherapy circuitry to target skeletal musculature at high intensity as the time at which the HVT is to be applied approaches; and
thereafter, cause electrotherapy circuitry to apply the HVT to the patient via the patient interface.

11. The electrotherapy device of claim 1, wherein the hemodynamic sensor is configured to measure at least one hemodynamic condition selected from the group consisting of: blood flow, blood pressure, blood oxygenation, or any combination thereof.

12. The electrotherapy device of claim 1, wherein the hemodynamic sensor includes at least one sensor selected from the group consisting of: a pulse oximeter, a sonic arterial pulse sensor, a gas sensor, a blood pressure sensor, a impedance measuring arrangement, or any combination thereof.

13. The electrotherapy device of claim 1, wherein cardiac output monitoring circuitry is configured to distinguish between hemodynamic conditions of forced pulse output and return, and wherein the controller is configured to adjust the MVT parameters in response to detected differences in the hemodynamic conditions of forced pulse output and return.

14. The electrotherapy device of claim 13, wherein the controller is configured to such that:
in response to an indication of weak return but adequately high pulse pressure to meet the treatment or life-support objective, the MVT is adjusted to enhance and prolong the targeting of muscles that tend to expand the chest cavity, thereby lowering pressure around the heart to help draw in more blood; and
in response to a strong return but weak pulse the MVT is adjusted to extend the pulse train duration to force the heart to stay contracted for a longer period of time.

15. The electrotherapy device of claim 1, wherein the device is configured to modulate the pulse period of the MVT.

16. The electrotherapy device of claim 1, wherein the patient monitoring circuitry is configured to detect pulseless electrical activity (PEA) in the patient, and wherein the controller is configured to respond to detection of PEA by causing the electrotherapy circuit to apply MVT synchronized with a measured electrocardiogram (ECG) signal.

17. The electrotherapy device of claim 1, wherein the MVT pulse generator is constructed such that the train repetition rate is adjustable within the range of 30 and 120 per minute, the pulse width is adjustable within the range of 0.15 and 10 milliseconds and an the pulse period is adjustable within the range of 5 and 70 milliseconds.

18. The electrotherapy device of claim 1, wherein the MVT pulse generator is constructed such that a pulse current of the MVT delivered to the patient falls within the range of 0.25 and 5 amperes.

19. The electrotherapy device of claim 1, wherein the controller is configured to cause the electrotherapy circuitry to apply a first MVT waveform targeting the first muscle group and, immediately thereafter, apply a second MVT waveform targeting the second muscle group such that the musculature of the first muscle group and the second muscle group continuously maintain compression of the heart.

* * * * *